United States Patent
Valaie

(10) Patent No.: US 9,205,244 B2
(45) Date of Patent: Dec. 8, 2015

(54) HAEMOSTATIC VALVE DEVICE

(75) Inventor: Arman H. Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 903 days.

(21) Appl. No.: 13/379,961

(22) PCT Filed: Jun. 29, 2010

(86) PCT No.: PCT/US2010/040380
§ 371 (c)(1),
(2), (4) Date: Jan. 26, 2012

(87) PCT Pub. No.: WO2011/008537
PCT Pub. Date: Jan. 20, 2011

(65) Prior Publication Data
US 2012/0130354 A1     May 24, 2012

Related U.S. Application Data

(60) Provisional application No. 61/221,343, filed on Jun. 29, 2009.

(51) Int. Cl.
*A61M 39/06*     (2006.01)

(52) U.S. Cl.
CPC ....... *A61M 39/0693* (2013.01); *A61M 39/0606* (2013.01); *A61M 2039/0633* (2013.01); *A61M 2039/0653* (2013.01)

(58) Field of Classification Search
CPC ............ A61M 39/06; A61M 39/0613; A61M 39/0606; A61M 39/0693; A61M 2039/0653; A61M 2039/0633
USPC ............. 604/167.01, 167.02, 167.03, 167.04, 604/167.05, 167.06, 164.04, 164.05, 604/288.02, 103.03, 278, 256, 251, 237; 277/630, 637
See application file for complete search history.

(56) References Cited

U.S. PATENT DOCUMENTS

| | | |
|---|---|---|
| 1,862,283 A | 6/1932 | Schoetzow |
| 2,321,336 A | 6/1943 | Tondreau |

(Continued)

FOREIGN PATENT DOCUMENTS

| | | |
|---|---|---|
| EP | 0247824 | 12/1987 |
| EP | 369314 | 5/1990 |

(Continued)

OTHER PUBLICATIONS

International Search Report and Written Opinion for PCT/US2010/040380 dated Nov. 3, 2010, 16 pgs.

(Continued)

*Primary Examiner* — Kami A Bosworth
*Assistant Examiner* — Hamza Darb
(74) *Attorney, Agent, or Firm* — Brinks Gilson & Lione

(57) ABSTRACT

A haemostatic valve device (10) comprises a disk valve (52a) having a valve body with a first surface facing in a first direction, a second surface facing in a second direction opposite the first direction, and an opening (58a) formed in the valve body for providing communication through the disk valve. In some examples, the disk valve comprises a nipple (60b), axially offset from the opening, extending outwardly and away from at least one of the first and second surfaces. The haemostatic valve device may further comprise a second disk valve (52b) and the nipple (60b) may be removably disposed within, and sealingly engage, an opening (58b) of the second disk valve.

9 Claims, 8 Drawing Sheets

(56) References Cited

U.S. PATENT DOCUMENTS

| | | |
|---|---|---|
| 2,416,391 A | 2/1947 | Hixson |
| 3,185,179 A | 5/1965 | Harautuneian |
| 3,304,934 A | 2/1967 | Bautista |
| 3,329,390 A | 7/1967 | Hulsey |
| 3,599,637 A | 8/1971 | Schwartz |
| 4,000,739 A | 1/1977 | Stevens |
| 4,016,879 A | 4/1977 | Mellor |
| 4,063,555 A | 12/1977 | Ulinder |
| 4,243,034 A | 1/1981 | Brandt |
| 4,311,137 A | 1/1982 | Gerard |
| 4,314,555 A | 2/1982 | Sagae |
| 4,424,833 A | 1/1984 | Spector et al. |
| 4,430,081 A | 2/1984 | Timmermans |
| 4,540,411 A | 9/1985 | Bodicky |
| 4,580,573 A | 4/1986 | Quinn |
| 4,610,665 A | 9/1986 | Matsumoto et al. |
| 4,610,674 A | 9/1986 | Suzuki et al. |
| 4,626,245 A | 12/1986 | Weinstein |
| 4,629,450 A | 12/1986 | Suzuki et al. |
| 4,798,594 A | 1/1989 | Hillstead |
| 4,895,565 A | 1/1990 | Hillstead |
| 4,929,235 A | 5/1990 | Merry et al. |
| 4,932,633 A | 6/1990 | Johnson et al. |
| 4,978,341 A | 12/1990 | Niederhauser |
| 5,000,745 A | 3/1991 | Guest et al. |
| 5,006,113 A | 4/1991 | Fischer |
| 5,009,391 A | 4/1991 | Steigerwald |
| 5,053,013 A | 10/1991 | Ensminger et al. |
| 5,066,285 A | 11/1991 | Hillstead |
| 5,102,395 A | 4/1992 | Cheer et al. |
| 5,125,903 A | 6/1992 | McLaughlin et al. |
| 5,154,701 A | 10/1992 | Cheer et al. |
| 5,158,553 A | 10/1992 | Berry et al. |
| 5,167,637 A | 12/1992 | Okada et al. |
| 5,176,652 A | 1/1993 | Littrell |
| 5,211,370 A | 5/1993 | Powers |
| 5,242,413 A | 9/1993 | Helliger |
| 5,256,150 A | 10/1993 | Quiachon et al. |
| 5,267,966 A | 12/1993 | Paul |
| 5,300,032 A | 4/1994 | Hibbs et al. |
| 5,304,156 A | 4/1994 | Sylvanowicz et al. |
| 5,350,363 A | 9/1994 | Goode et al. |
| 5,350,364 A | 9/1994 | Stephens et al. |
| 5,356,381 A * | 10/1994 | Ensminger et al. ...... 604/288.03 |
| 5,376,077 A | 12/1994 | Gomringer |
| 5,395,349 A | 3/1995 | Quiachon et al. |
| 5,395,352 A | 3/1995 | Penny |
| 5,409,463 A | 4/1995 | Thomas et al. |
| 5,484,418 A | 1/1996 | Quiachon et al. |
| 5,538,505 A | 7/1996 | Weinstein et al. |
| 5,613,956 A | 3/1997 | Patterson et al. |
| 5,643,227 A | 7/1997 | Stevens |
| 5,653,697 A | 8/1997 | Quiachon et al. |
| 5,702,370 A | 12/1997 | Sylvanowicz et al. |
| 5,779,681 A | 7/1998 | Bonn |
| 5,895,376 A | 4/1999 | Schwartz et al. |
| 5,927,725 A * | 7/1999 | Tabata et al. ................ 277/607 |
| 5,935,122 A | 8/1999 | Fourkas et al. |
| 6,086,570 A | 7/2000 | Aboul-Hosn et al. |
| 6,179,863 B1 | 1/2001 | Kensey et al. |
| 6,197,016 B1 | 3/2001 | Fourkas et al. |
| 6,221,057 B1 | 4/2001 | Schwartz et al. |
| 6,276,661 B1 | 8/2001 | Laird |
| 6,379,372 B1 | 4/2002 | Dehdashtian et al. |
| 6,416,499 B2 | 7/2002 | Paul, Jr. |
| 6,562,049 B1 | 5/2003 | Norlander et al. |
| 6,610,031 B1 | 8/2003 | Chin |
| 6,652,480 B1 | 11/2003 | Imran et al. |
| 6,966,896 B2 | 11/2005 | Kurth et al. |
| 6,981,966 B2 | 1/2006 | Green et al. |
| 7,172,580 B2 | 2/2007 | Hruska et al. |
| 7,182,771 B1 | 2/2007 | Houser et al. |
| 7,226,433 B2 | 6/2007 | Bonnette et al. |
| 7,241,276 B2 | 7/2007 | Argentine et al. |
| 7,351,247 B2 | 4/2008 | Kupiecki et al. |
| 2003/0144670 A1 | 7/2003 | Pavcnik et al. |
| 2003/0216771 A1 | 11/2003 | Osypka et al. |
| 2004/0111060 A1* | 6/2004 | Racenet et al. .......... 604/167.01 |
| 2005/0096605 A1 | 5/2005 | Green et al. |
| 2005/0171479 A1 | 8/2005 | Hruska et al. |
| 2006/0052750 A1 | 3/2006 | Lenker et al. |
| 2007/0078395 A1 | 4/2007 | Valaie |
| 2008/0157017 A1 | 7/2008 | Mccatangay et al. |
| 2010/0305496 A1* | 12/2010 | Kuebler et al. ................. 604/22 |

FOREIGN PATENT DOCUMENTS

| | | |
|---|---|---|
| EP | 0 550 069 A1 | 7/1993 |
| EP | 0 344 907 B1 | 9/1998 |
| EP | 1 374 942 B1 | 8/2006 |
| EP | 0 755 694 B1 | 9/2006 |
| GB | 1503429 | 3/1978 |
| WO | WO 99/26682 A1 | 6/1999 |
| WO | WO2007/030746 | 3/2007 |

OTHER PUBLICATIONS

Communication Pursuant to Article 94(3) EPC Action for related European Application No. 10 743 270.0, dated Jan. 20, 2015, 6 pgs.

* cited by examiner

HAEMOSTATIC VALVE DEVICE

RELATED APPLICATIONS

The present patent document is a §371 filing based on PCT Application Serial No. PCT/US2010/040380, filed Jun. 29, 2010 (and published as WO 2011/008537 A1 on Jan. 20, 2011), designating the United States and published in English, which claims the benefit of the filing date under 35 U.S.C. §119(e) of Provisional U.S. Patent Application Ser. No. 61/221,343, filed Jun. 29, 2009. All of the foregoing applications are hereby incorporated by reference in their entirety.

FIELD OF THE INVENTION

The present invention relates to haemostatic valves, devices, and systems, and methods of making and using same.

BACKGROUND OF THE INVENTION

Numerous procedures have been developed that involve the percutaneous insertion of a medical device into a vessel. Such a device may be introduced into the vessel by a variety of known techniques. For example, a wire guide may be introduced into a vessel using the Seldinger technique. This technique involves making a surgical opening in a vessel by a needle and inserting a wire guide into the vessel through a bore in the needle. The needle can be withdrawn, leaving the wire guide in place. An introducer device is then inserted over the wire guide and into the vessel. The introducer device may be used in conventional fashion to insert a variety of types of medical devices, such as catheters, cardiac leads, balloons, stents, stent grafts, and the like.

One of the challenges associated with endoluminal procedures is controlling the flow of bodily fluids within the introducer device during the procedure. Haemostatic devices and valve systems control the flow of blood through an introducer. US-A-2007/0078395 entitled "Haemostatic Valve System", the disclosure of which is incorporated herein by reference, discloses numerous examples of haemostatic valve devices and systems that use disk valves to control fluid flow. US-A-2007/0078395 discloses, among other things, disk valves with holes that are offset from the radial center of the disk. In some examples, a valve system includes several such disks, aligned so that the holes are not substantially overlapping. Additional valve disks may be added to improve the pressure rating of such a valve system.

Using a large number of disk valves to provide a desired seal can present challenges. For example, as the number of disk valves increases, the total force required to insert a medical device through the valve system may increase. In addition, even when the valves are in a "closed" configuration, the holes in the disk valves remain open and may provide a pathway for leakage through the haemostatic device.

SUMMARY OF THE INVENTION

The present invention seeks to provide an improved haemostatic valve, valve and medical introducer or deployment device incorporating such a valve.

According to an aspect of the present invention, there is provided a haemostatic valve device including a disk valve including a valve body with a first surface facing in a first direction, a second surface facing in a second direction opposite the first direction, an opening formed in the valve body for providing communication through the disk valve, and a nipple extending outwardly and away from at least one of the first and second surfaces; wherein the nipple is axially offset from the opening.

According to another aspect of the present invention, there is provided a haemostatic valve device including a first disk valve having a valve body with an opening therein for providing communication through the first disk valve; and a second disk valve having a valve body with an opening therein for providing communication through the second disk valve, and a plug removably disposed within, and sealingly engaging, the opening of the first disk valve to limit fluid flow through the first disk valve.

Various examples of valve devices and systems are described throughout the specification and depicted in the drawings. In one example, a haemostatic valve device is provided and comprises a disk valve having a valve body with a first surface facing in a first direction, a second surface facing in a second direction opposite the first direction, an opening formed in the valve body for providing communication through the disk valve, and a nipple extending outwardly and away from at least one of the first and second surfaces of the valve body.

Such a disk valve may be used, for example, in combination with a second disk valve to provide a haemostatic valve device with superior haemostatic properties. In these examples, the valves are arranged so that the nipple is removably disposed within, and sealingly engages, an opening of the second disk valve. The nipple acts as a stopper or plug for the opening of the second disk valve, thereby limiting fluid flow through the opening. A medical device, such as a guide wire, may be inserted through the opening of the second disk valve to displace the nipple, break the sealing engagement, and allow the wire to pass through the openings. Such devices have a more robust sealing structure and may result in a better pressure rating than devices that use only traditional disk valves.

In some embodiments, the nipple has a tapered contour. The nipple may be attached to the valve body by any means. For example, the nipple and the valve body may comprise a monolithic structure. In examples comprising a second disk valve, the second disk valve may comprise a nipple that is removably disposed within, and sealingly engages, the opening of the first disk valve.

In another embodiment, a haemostatic valve device is provided and comprises a first disk valve and a second disk valve. Each disk valve has a valve body with an opening formed in the valve body for providing communication through the disk valve. The second disk valve may have a plug removably disposed within, and sealingly engaging, the opening of the first disk valve to limit fluid flow through the first disk valve. The first disk valve may, likewise, have a plug removably disposed within, and sealingly engaging, the opening of the second disk valve. In preferred examples, the opening of the first disk valve is axially offset from the opening of the second disk valve.

Guiding a device through first and second openings in such devices can be more challenging than in examples where the openings are axially aligned. Therefore, structures are disclosed herein for guiding a medical device between the first and second openings. For example, the plug of the second disk valve may have a dent with a contour that slopes towards the opening of the second disk valve. The plug of the second disk valve and the opening of the first disk valve may cooperate to form a niche having a contour that slopes towards the opening of the second disk valve. When a medical device, for example a guide wire, is inserted into the chamber, the dent and/or niche acts as a locator for the sealed opening of the first disk valve, biases the manner in which the medical device passes through the opening, and causes the opening to stretch in a predetermined direction, thereby deflecting and guiding the medical device towards the opening of the second disk valve.

BRIEF DESCRIPTION OF THE DRAWINGS

Embodiments of the present invention are described below, by way of example only, with reference to the accompanying drawings, in which.

TERMINOLOGY

Throughout the specification, when referring to a medical device, or a portion of a medical device, the terms "distal" and "distally" shall denote a position, direction, or orientation that is generally towards, or in the direction of, the patient when the device is in use. The terms "proximal" and "proximally" shall denote a position, direction, or orientation that is generally away from the patient, or closer to the operator, during use of the device.

The term "medical device" refers to any device, object, or structure, that supports, repairs, or replaces, is configured to support, repair, or replace, or that may be used, alone or in combination with other devices, objects, or structures, to support, repair, or replace a body part or a function of that body part. Examples of medical devices include, but are not limited to, sheaths, catheters, guide wires, cardiac leads, vessel occlusion devices, filters, stents, stent grafts, and delivery and deployment devices.

The term "opening" includes one or more apertures, perforations, gaps, spaces, holes, slits, slots, or the like.

The term "monolithic" refers to structures, or portions of structures, that are formed as a single integral piece, rather than being separately formed and attached.

The term "disk" describes structures with circular contours, as well as structures with contours that would not be described as circular (such as square, octagonal, and the like). Thus, the term "disk valve" describes valve structures that are circular, as well as structures that are not circular.

The term "niche" refers to a dent, detent, depression, cut, score, notch, line, recess, dimple, or other like structure in a surface.

DESCRIPTION OF THE PREFERRED EMBODIMENTS

Figure 1:
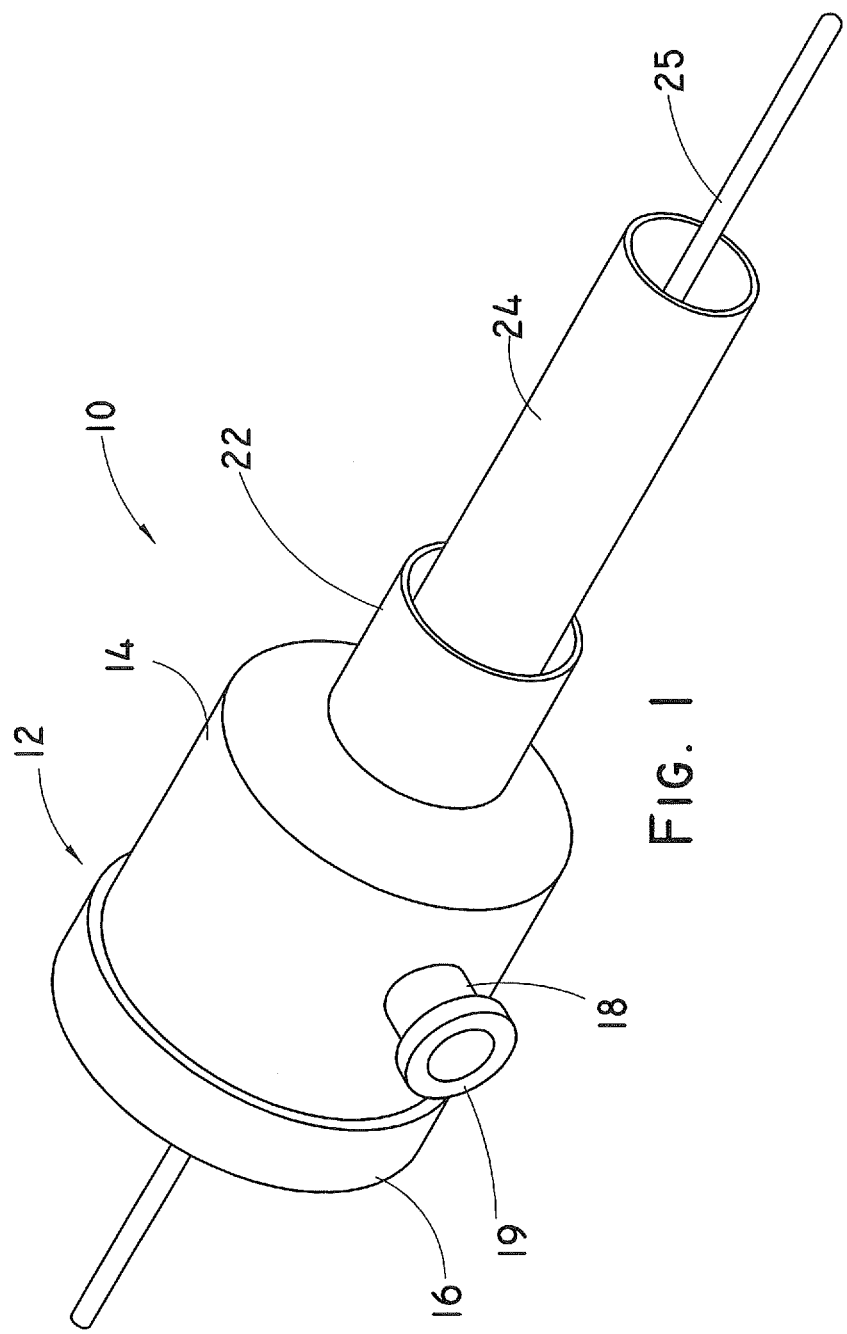
FIG. 1 is a perspective view of a haemostatic device.
Figure 2:
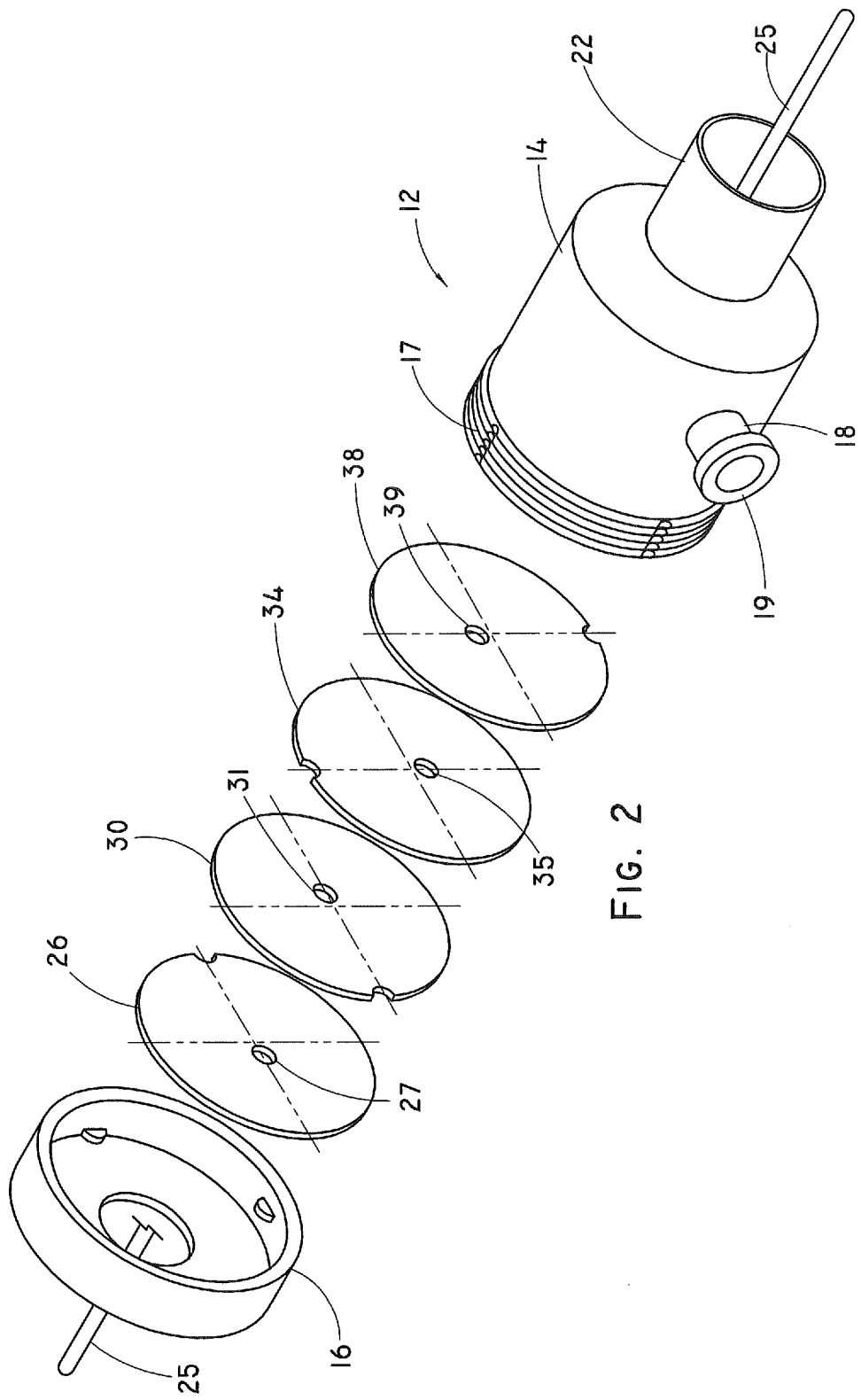
FIG. 2 is an exploded view of the device shown in FIG. 1.

FIGS. 1 and 2 illustrate a perspective view and exploded view, respectively, of one embodiment of introducer device 10. Various features of this device are described in detail in US-A-2007/0078395 where more specific details can be found. The device 10 includes a valve housing 12 having a main body 14 and an end cap 16. Main body 14 and end cap 16 may be joined in any conventional fashion, such as by a screw fit or a snap fit. AS can be seen in FIG. 2, main housing body 14 has one or more screw threads 17 that correspond with a lip or other suitable structure in the end cap. Housing 12 may also include a side-arm spout 18 extending in a generally transverse direction from main housing body 14. Spout 18 may be used for transmitting or aspirating a fluid or drug in a conventional fashion, and preferably includes a lip 19 sized and shaped for threaded or like engagement with a tube or other device (not shown). The distal end of main housing body 14 comprises a smaller diameter portion 22. A removable sheath 24 extends distally from smaller diameter portion 22 of housing 12 in conventional fashion. A wire guide 25 extends through device 10.

The device comprises a plurality of disk valves 26, 30, 34, 38, as shown in FIG. 2, disposed within a chamber of the housing 12. The valves 26, 30, 34, 38 are axially aligned between main body 14 and end cap 16. Each valve has an opening 27, 31, 35, 39 (depicted, in this example, as a generally circular hole) that allows communication through the valve of fluids, such as blood. The openings 27, 31, 35, 39 are preferably sized to enable communication or passage of a medical device, such as a catheter. In this example, the openings are each axially offset from the radial center of the respective disk. To improve the pressure rating of the valve system, the valves are arranged so that openings in immediately adjacent disks are not substantially overlapping. The device shown in FIGS. 1 and 2 includes numerous other features that are described in US-A-2007/0078395.

The use of disks in haemostatic valve systems is well known. The disks preferably comprise a material with sufficient elasticity to enable an opening formed in the disk to stretch to the extent required to allow a medical device to pass through the disk, and to enable the disk and opening to substantially return to a pre-stretched condition when the medical device is removed. Examples of suitable materials include silicone and urethane, although any other suitable composition known in the art for such purposes may also be used.

Figure 3:
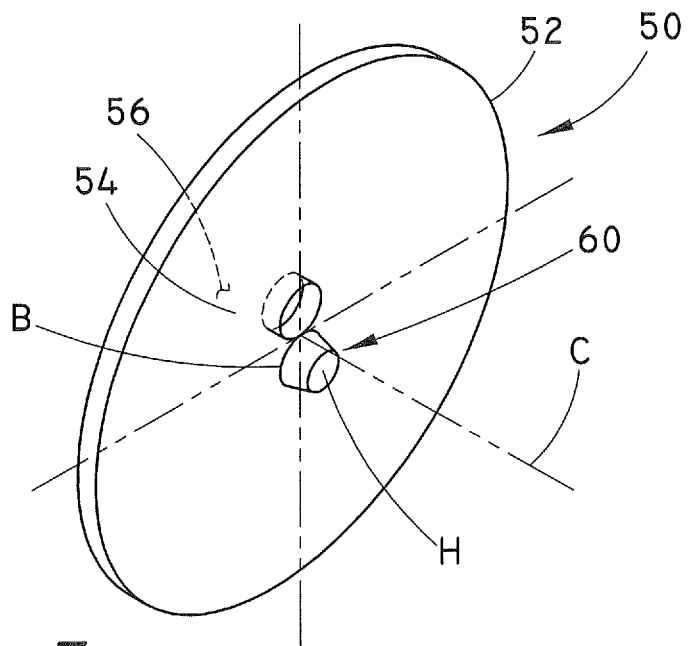
FIG. 3 is a perspective view of an embodiment of valve device.

FIG. 3 depicts an embodiment of disk valve 50 that may be used along with, or instead of, a conventional disk valve. The valve 50 includes a valve body 52 having a first surface 54 facing a first direction, a second surface 56 facing a second direction, opposite the first direction, and an opening 58 between the first and second surfaces. The valve body 52 preferably comprises an elastic material, as described above, and is fluid impermeable.

Opening 58 provides a path for communication through the valve 50. Opening 58 is preferably sized and configured to allow passage of a medical device (not shown) through the valve 50, as described above. In some examples, opening 58 may have a generally circular shape and have an unexpanded diameter of approximately 0.1 mm. Such an opening may expand to 50 or 60 times its diameter, depending on the elasticity of the disk material. In other embodiments, opening may have a non-circular shape and/or may have an unexpanded dimension that is less than, or greater than, 0.1 mm.

In the embodiment of FIG. 3, opening 58 is axially offset from the radial center C of the valve body 52. In other embodiments, valve 50 may have an opening disposed at the radial center of the valve body. Opening 58 is depicted in FIG. 3 as a generally circular aperture, however other structures and configurations are also contemplated. For example, opening may comprise one or more slits.

Disk valve 50 has a nipple 60 that extends outwardly and away from the first surface 54 of the valve body 52. Nipple 60 has a base B attached to the valve body 52 and extends outwardly towards head H (see FIG. 7A). Nipple 60 and opening 58 are each axially offset from the radial center C of the valve body 52 and are axially offset from each other. The distance between nipple 60 and opening 58 may vary by design. Thus, in some examples, nipple 60 and opening 58 may be axially aligned.

Nipple 60 is sized and configured to engage and seal an opening in a valve to limit communication through the valve (described further below). The shape, size, and configuration of the nipple can vary. To facilitate engagement of the nipple 60 with the opening, the head H preferably has a radial dimension that is less than, or equal to, the radial dimension of the opening to be sealed (see for example FIG. 4, described below). To facilitate sealing, at least a portion of the nipple should preferably have a radial dimension that is equal to, or greater than, the radial dimension of the opening to be sealed. This "sealing" region is denoted in FIG. 7A as "S."

Figure 7A:
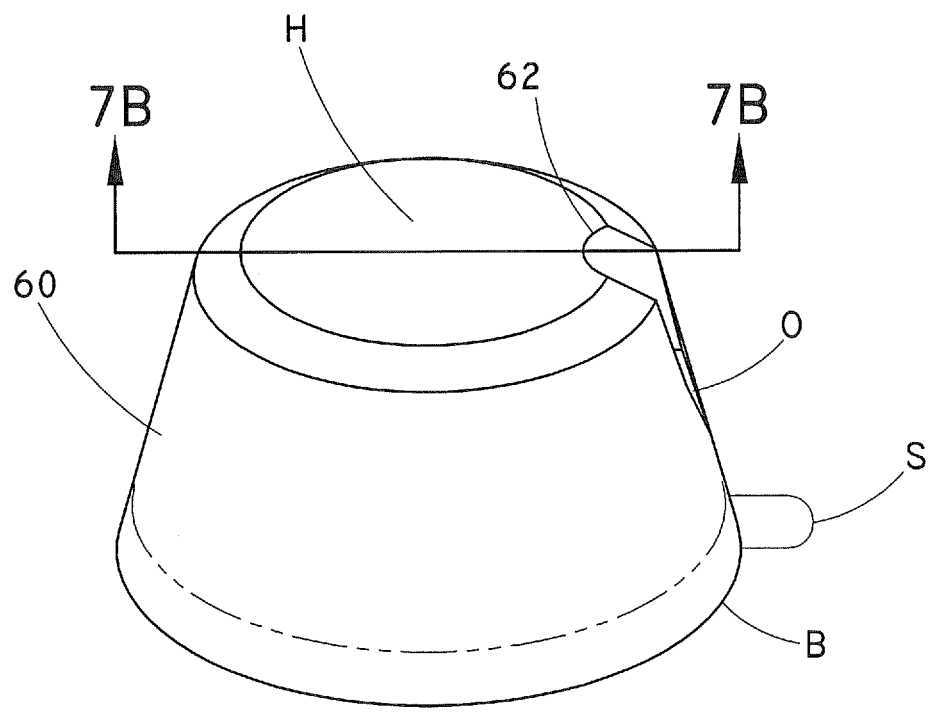
FIG. 7A is a perspective view of an embodiment of nipple for the valve devices disclosed herein.
Figure 7B:
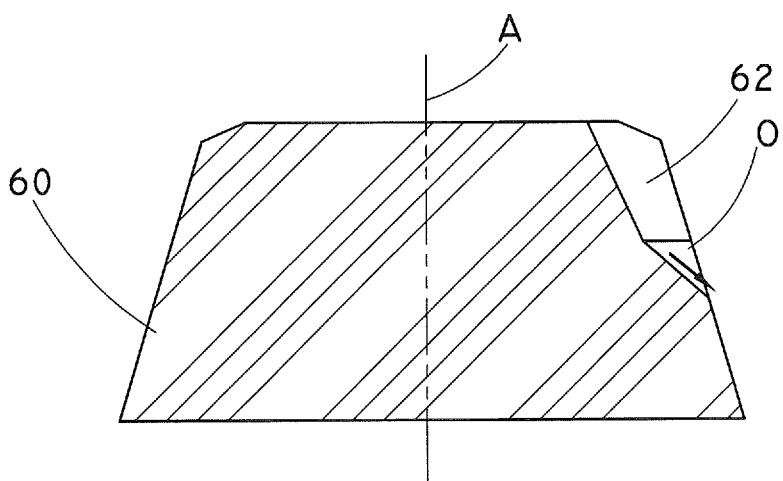
FIG. 7B is a cross-sectional view of the nipple of FIG. 7A.

In the embodiments of FIGS. 3, 7A, and 7B, the nipple 60 is generally frustoconical and has a diameter that increases towards the base B. The cone or frustum may have a circular cross-section, as shown, or a non-circular cross-section (for example, a square contour). In some examples, a nipple may be provided with a "snap-fit" structure (not shown), such as one or more annular depressions, ridges, crests, or the like, that cooperate with a valve opening to form a reversible mechanical interlock between the nipple and opening. Such a structure may further enhance the integrity of the seal.

Nipple 60 may be attached to the valve body 52 by conventional means such as fusing, welding, adhering, or the like. In preferred examples, the nipple 60 and valve body 52 have a monolithic structure and may be formed, for example, by casting, molding, thermoforming, pressure forming, or like technique.

Figure 4:
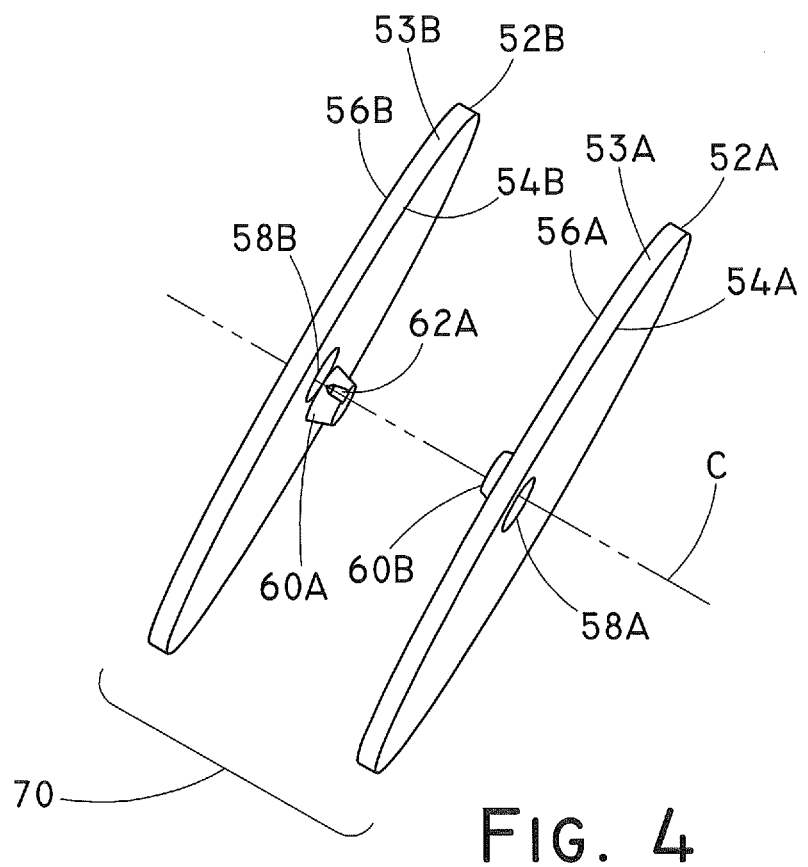
FIG. 4 is a perspective view of another embodiment valve device.

FIG. 4 depicts an exploded view of a valve device 70 with disk valves 52A, 52B. Valve 52A comprises a valve body 53A having a first surface 54A, a second surface 56A, and an opening 58A between the first and second surfaces. Valve 52B comprises a valve body 53B having a first surface 54B, second surface 56B, and opening 58A between the first and second surfaces. Openings 58A, 58B are each axially offset from the radial center C of the disks 52A, 52B. Each valve body 53A, 53B comprises a nipple 60B, 60A. The valves 52A, 52B are arranged so that nipple 60A is axially aligned with opening 58A and nipple 60B is axially aligned with opening 58B. In this arrangement, nipples 60A, 60B each define a plug that is capable of entering, and sealingly engaging, a respective opening 58A, 58B. The nipples 60A, 60B are each designed so that, in use, their length is at least equal to the spacing distance D (shown in FIG. 6) between valves 52A, 52B. In preferred examples, each nipple has a length that is greater than the spacing distance D. In some examples, a nipple may be provided with a length of 0.1 mm or greater, 0.2 mm or greater, or 0.5 mm or greater.

Figure 5:
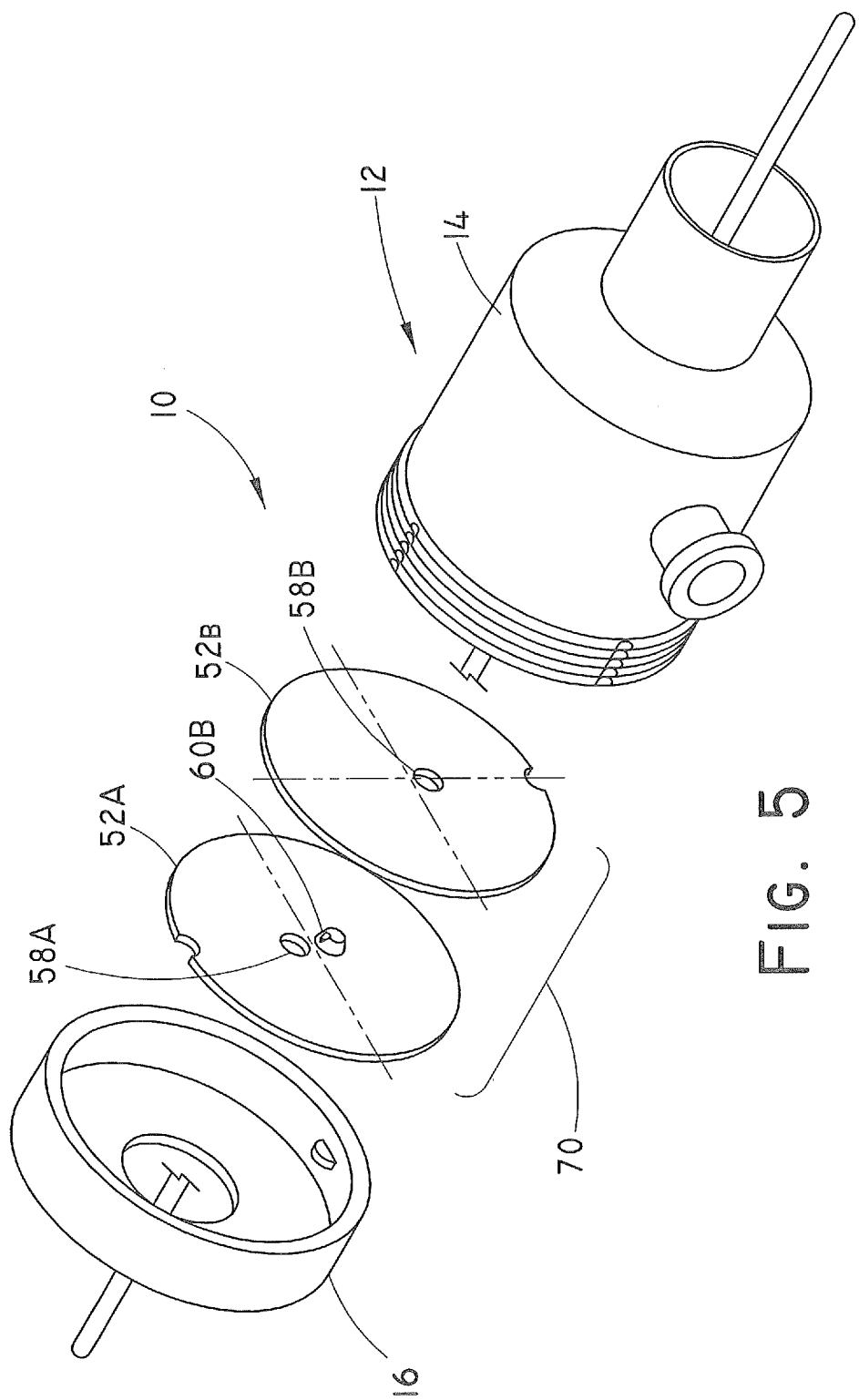
FIG. 5 is an exploded view of an embodiment of haemostatic device including a valve device similar to the one shown in FIG. 4.

FIG. 5 depicts an exploded view of a device 10, similar to the introducer device depicted in FIGS. 1 and 2 that includes a valve 70, similar to the valve depicted in FIG. 4. In this example, two disk valves 52A, 52B are used instead of the four disk valves depicted in FIG. 2. Valves 52A, 52B are arranged so that nipple 60A (hidden) is axially aligned with opening 58A and nipple 60B is axially aligned with opening 58B. Valves 52A, 52B are assembled within the valve housing 12 in relatively close proximity so that nipple 60A can plug opening 58A and nipple 60B can plug opening 58B. In use, fluid pressure within the haemostatic device 10 forces the valves 52A, 52B into intimate contact so that plug 60A penetrates and covers the perimeter of opening 58A and plug 60B penetrates and covers the perimeter of opening 58B.

Figure 6:
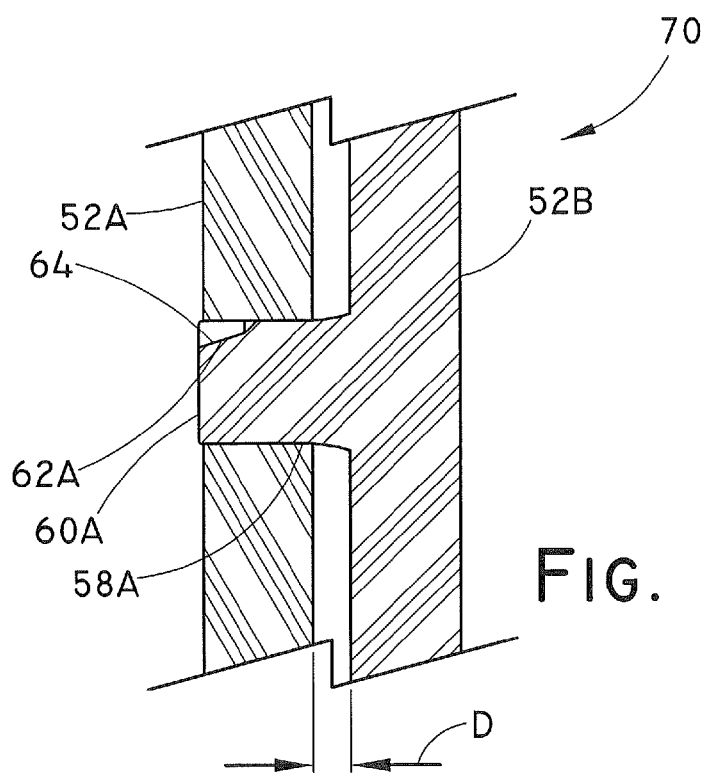
FIG. 6 is a cross-sectional view of the valve device shown in FIG. 4.

FIG. 6 depicts a cross-sectional view of a portion of valve device 70 with nipple 60A removably disposed within, and sealingly engaging, valve opening 58A. This sealing structure results in a more robust seal between valves 52A, 52B than is possible with previously-known disk valves only, where fluid pockets may form due to decreased surface tension between the disks. As a result of this unique sealing structure, a two-body valve, like the one depicted in FIG. 4, may have an improved pressure rating over a device using two, three, four, or more previously-known disk valves.

Figure 8:
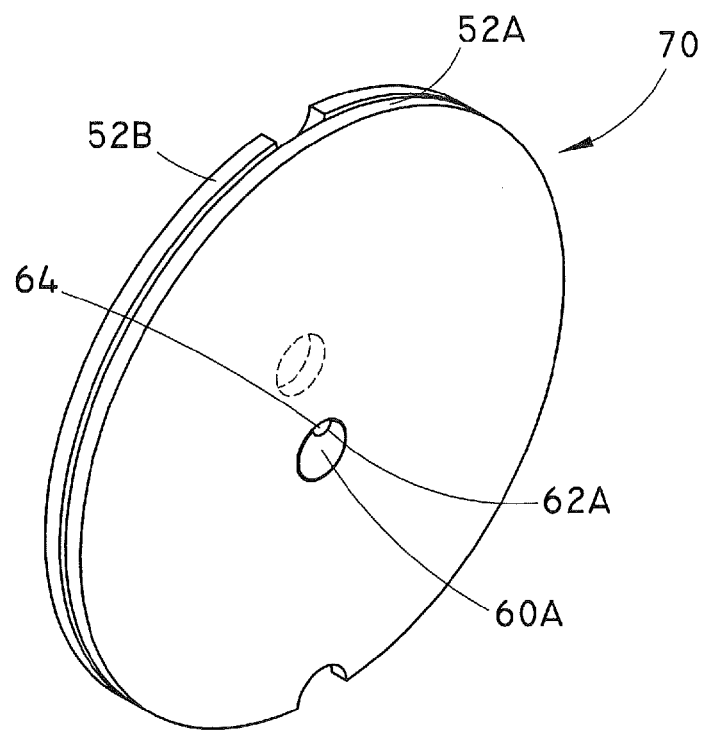
FIG. 8 is a perspective view of the valve device shown in FIG. 4.

In the embodiments shown in FIGS. 4 and 5, opening 58A is axially offset from opening 58B. These unaligned openings may present a challenge to the operator in navigating a medical device along multiple axes through the valve assembly. To facilitate this, the valve 70 system preferably has a structure that can guide a medical device between adjacent openings 58A, 58B. For example, nipple 60A may have a dent 62 (shown in FIGS. 4, 7A, and 7B) with a contour O that slopes outwardly and away from the center axis A of the nipple and towards opening 58B (see also FIGS. 7 and 7A). In the embodiment shown in FIGS. 7A and 7B, dent 62 has a tapered conical contour, although other contours may be provided or desired. Nipple 60A and opening 58A may cooperate to form a niche 64, as shown in FIG. 8. Niche 64 is formed by the adjacent radial surfaces of the dent 62A and opening 58A. In other embodiments, an opening may be provided with a dent (not shown), and a niche may be formed by adjacent radial surfaces of the dent and nipple.

Dent 62A and niche 64 facilitate guiding a medical device, such as a guide wire, between openings 58A, 58B. In particular, the niche 64 structure is designed to locate and receive at least a portion of the medical device. Once the device is received in the niche 64, the dent 62A deflects it outwardly, and towards opening 58B. This causes opening 58A to stretch in a predetermined direction towards opening 58B.

FIGS. 9A-9D depict a haemostatic valve device 10 in stages of use. The device includes a valve housing 12 and two disk valves 52A, 52B disposed within the housing. Valve 52A comprises a nipple 60B that is removably disposed within, and sealingly engages, opening 58B of valve 52B. Likewise, valve 52B comprises a nipple 60A that is removably disposed within, and sealingly engages, opening 58A of valve 52A. Each of the nipples 60A, 60B has a dent 62A, 62B which, in cooperation with openings 58A, 58B, defines a niche 64A, 64B.

Figure 9A:
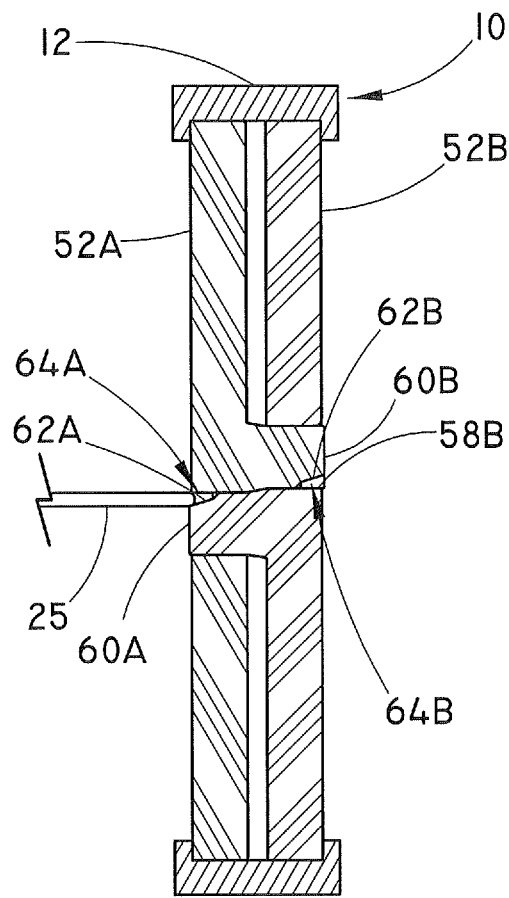
FIGS. 9A-9D depict various views of a valve device in stages of use.

FIG. 9A depicts the valves in a sealing configuration where nipple 60A sealingly engages opening 58A, and nipple 60B sealingly engages opening 58B, to limit fluid flow through the device. A guide wire 25 is shown disposed within the housing 12 and the tip of the guide wire is received within niche 64A. When the guide wire 25 is pushed through opening 58A, dent 62A deflects and guides the tip of the guide wire toward and through opening 58B.

Figure 9B:
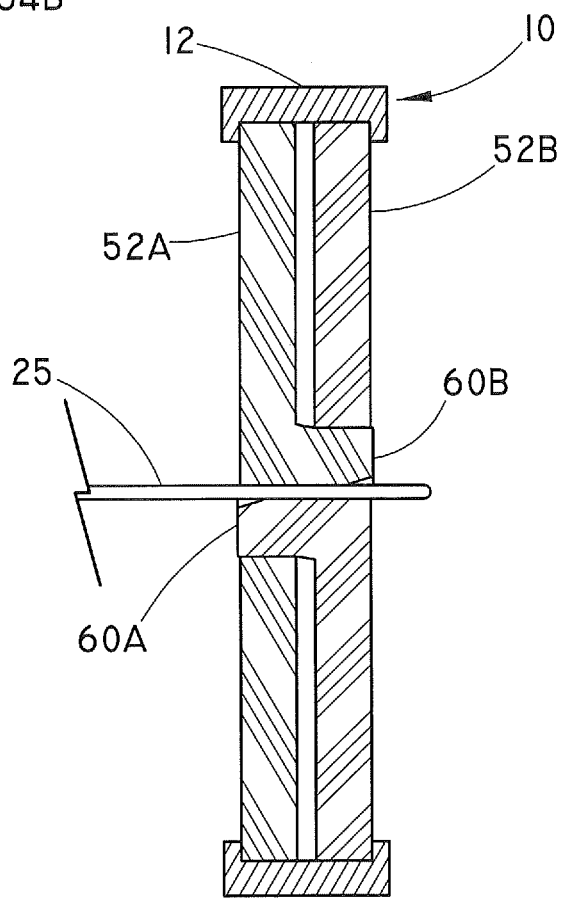
Figure 9C:
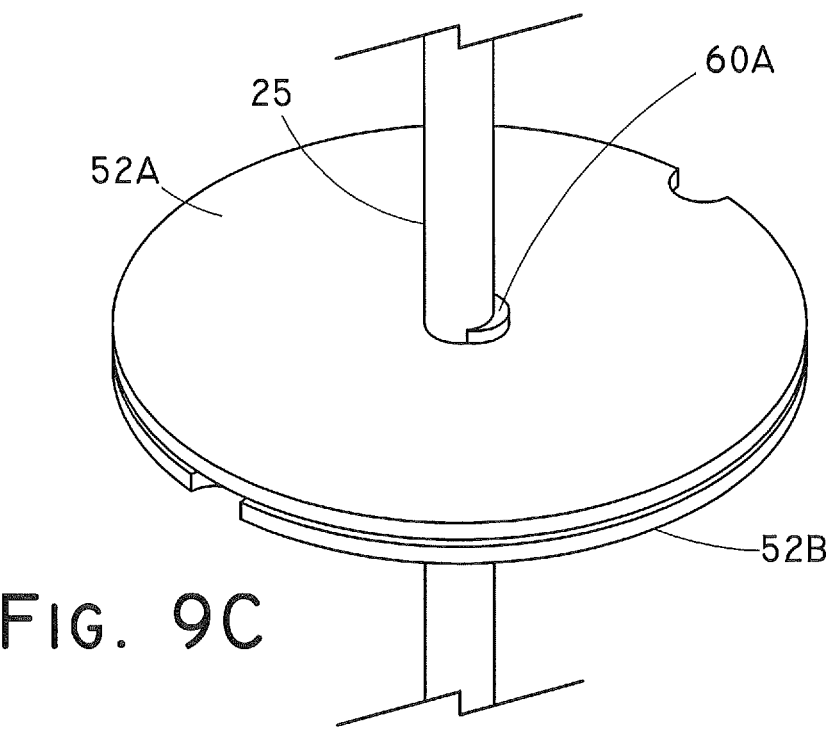
Figure 9D:
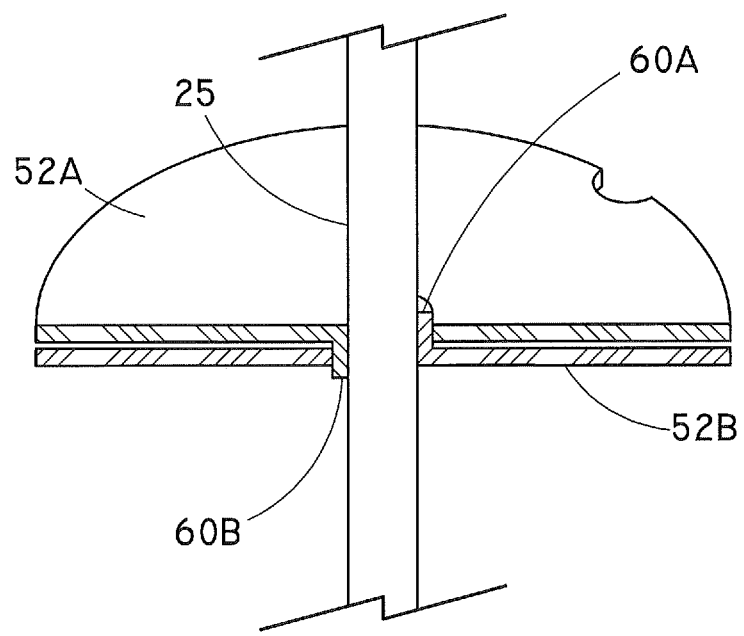

In FIG. 9B, the guide wire 25 is pushed through valve openings 58A, 58B, and displaces nipples 60A, 60B, thereby breaking the sealing engagement between nipples 60A, 60B and openings 58A, 58B. The wire 25 stretches opening 58A radially in the direction of opening 58B and opening 58B radially in the direction of opening 58A. The openings 58A, 58B deform about the wire 25 and create two opposing generally parabolic shapes that seal the curvature of the wire. The nipples 60A, 60B are displaced and, in some examples, may slide behind the facing valve. FIGS. 9C and 9D depict views of the valve system with guide wire 12 passing through the valves 52A, 52B.

When the guide wire 25 is removed from the valve device, the openings 58A, 58B relax and contract towards their unexpanded configurations. As the openings contract, the nipples 60A, 60B sealingly engage a respective opening 58A, 58B, preventing fluid flow through the disks and, thereby, sealing the valve system. Due to their designed contour (shown, for example, in FIGS. 7A and 7B), the nipples 60A, 60B will fall in place naturally. Moreover, any pressure on either valve (such as fluid pressure on valve 58B) will tend to force the nipples 60A, 60B into further engagement with the openings 58A, 58B, further improving the seal.

Throughout this specification various indications have been given as to preferred and different embodiments of the invention. However, it should be understood that the invention is not limited to any one of these. It is therefore intended that the foregoing detailed description be regarded as illustrative rather than limiting. Moreover, the features of different embodiments may be combined together as no embodiment described above is intended to be an alternative of another.

It is to be understood that although the examples described above show the nipples being spaced from the apertures on the same disk, in some embodiments the nipples may be immediately adjacent these apertures. Such an arrangement provides a less tortuous path through the valve assembly for, for instance, a medical device.

The disclosures in U.S. patent application No. 61/221,343, from which this application claims priority, and in the abstract accompanying this application are incorporated herein by reference.

The invention claimed is:

1. A haemostatic valve device comprising:
a first disk valve having a valve body with a first surface facing in a first direction, a second surface facing in a second direction opposite the first direction, a stretchable opening formed in the valve body for providing communication through the disk valve, and a nipple extending outwardly and away from at least one of the first and second surfaces, where the nipple is axially offset from the opening; and
a second disk valve having a valve body with a first surface facing in the first direction, a second surface facing in the second direction opposite the first direction, and a stretchable opening formed in the second valve body for providing communication through the second disk valve, where the first and second disk valves are arranged so that the nipple is removably disposed within, and sealingly engages, the opening of the second disk valve.

2. The device of claim 1 where the second disk valve further comprises a nipple, and where the second disk valve nipple is removably disposed within the opening of the first disk valve.

3. The device of claim 2 wherein the second disk valve nipple substantially sealingly engages the opening of the first disk valve.

4. The device of claim 1 where the first and second disk valves are separated by a spacing distance, and the nipple has a length that is equal to, or greater than, the spacing distance.

5. The device of claim 1 where the nipple and the first disk valve body comprise a monolithic structure.

6. The device of claim 1 where the nipple has a tapered contour.

7. A haemostatic valve device comprising:
a disk valve having a valve body with a first surface facing in a first direction, a second surface facing in a second direction opposite the first direction, a stretchable opening formed in the valve body for providing communication through the disk valve, and a nipple extending outwardly and away from at least one of the first and second surfaces, where the nipple is axially offset from the opening and comprises a dent having a contour that slopes towards the opening.

8. The device of claim 1 where the nipple is generally frusto-conical in shape.

9. The device of claim 1 where the nipple extends a distance of 0.1 mm or greater from the surface of the first disk valve and towards the opening of the second disk valve.

* * * * *